United States Patent [19]
Tomaru et al.

[11] Patent Number: 5,869,044
[45] Date of Patent: Feb. 9, 1999

[54] METHOD FOR THE TREATMENT OR PROPHYLAXIS OF ISCHEMIA-REPERFUSION INJURY

[75] Inventors: Takanobu Tomaru, Tokyo, Japan; Pei-Gen Kuang, Beijing, China

[73] Assignee: Tobishi Pharmaceutical Co., Ltd., Tokyo, Japan

[21] Appl. No.: 665,982

[22] Filed: Jun. 19, 1996

[30] Foreign Application Priority Data

Jun. 28, 1995 [JP] Japan ................................. 8-161665

[51] Int. Cl.⁶ ........................................... A61K 38/48
[52] U.S. Cl. ...................... 424/74.64; 424/542; 514/2; 530/350; 530/356
[58] Field of Search ................... 424/94.64, 542; 514/2; 530/350, 856

[56] References Cited

U.S. PATENT DOCUMENTS

| | | | |
|---|---|---|---|
| 3,849,252 | 11/1974 | Percs et al. ................................. | 195/62 |
| 5,135,004 | 8/1992 | Adams et al. ........................... | 128/696 |
| 5,453,359 | 9/1995 | Gargan et al. ............................. | 435/13 |
| 5,523,292 | 6/1996 | Schwartz et al. ......................... | 514/21 |
| 5,595,974 | 1/1997 | Tomaru ..................................... | 514/21 |

OTHER PUBLICATIONS

Dorland's Medical Dictionary, 27th Edition, pp. 857, 1579, 1988.
Lowe, G.D.O et al., Angiology, vol. 33(1), pp. 46–50, Jan. 1982.
Queiroz, L.A. et al., Toxicon, vol. 23(1), p. 36, 1985.
Hospital Practice, vol. 9(8), p. 37, Aug. 1974.
Hartmann, J.R. et al., The American Journal of Cardiology, vol. 40(4), pp. 550–555, Oct. 1977.
Barrie, W.W. et al., Arch Surg., vol. 111(15), pp. 561–563, May 1976.
Bonilla, C.A. et al., American Heart Journal, vol. 90(1), pp. 43–49, Jul. 1975.
Tanahashi N. et al: "Effect of single intravenous administration of batroxobin on erythrocyte aggregability in patients with acute–stage cerebral infarction", Clinical Hemorheology, vol. 15, No. 1, 1995, USA, pp. 89–96, XP000197385, abstract, p. 90, line 1–line 10.
Gordon D.O. Lowe: "Defibrination, blood flow and blood rheology" Clinical Hemorheology, vol. 4, 1984, USA, pp. 15–28, XP000195919, p. 17, line 13–line 20, p. 20, line 11–line 29.
Latallo Z S: "International Committee Communications. Retrospective Study on Complications and Adverse Effects of Treatment with Thrombin–like Enzymes—A Multicentre Trial" Thrombosis and Haemostasis, vol. 50, No. 2, 1983, pp. 604–609, XP000197388, p. 605, left–hand col., line 15–line 26, p. 605; table 4.
Database Chemabs Chemical Abstracts Service, Columbus, Ohio, US AN: 117:205106, Namikata, Shohei et al: "Effects of snake venom batroxobin (defibrase) on cerebral infarction in a rat model", XP002045039, & Yakuri to Chiryo (1992), 20(7), 2393–405, abstract.
Nobuyuki Itoh, et al., "Molecular Cloning and Sequence Analysis of cDNA for Batroxobin, a Thrombin–like Snake Venom Enzyme", The Journal of Biological, Chemistry, vol. 262, No. 7 (pp. 3132–3135) Mar. 5, 1987.

*Primary Examiner*—Chhaya D. Sayala
*Attorney, Agent, or Firm*—Oblon, Spivak, McClelland, Maier & Neustadt, P.C.

[57] ABSTRACT

Medicaments for the treatment or prophylaxis of ischemia-reperfusion injury in myocardial ischemia and cerebral ischemia, characterized in that the medicament contains batroxobin as an effective component.

4 Claims, No Drawings

METHOD FOR THE TREATMENT OR PROPHYLAXIS OF ISCHEMIA-REPERFUSION INJURY

FIELD OF THE INVENTION

The present invention relates to a medicament for the treatment or prophylaxis of ischemia-reperfusion injury.

BACKGROUND OF THE INVENTION

Ischemia-reperfusion injury is a general term for an injury which occurs after blood circulation is restarted in an organic tissue fallen into ischemia when an excision operation or ablation of various organs is conducted. Such injury also occurs when blood circulation is restarted after being stopped for the transplantation of an organ. Thus, such an injury frequently occurs in many tissues, such as kidney, liver, lungs, pancreas and intestines as well as heart and brain.

So far, it has been believed that ischemia-reperfusion injury is caused by a rise in an energy metabolism or an increase in an active oxygen species by rapid reoxygenation, or a lipid peroxide and the like. However, the details of the mechanism still remain unknown. Under such circumstances, it is expected that if the active oxygen species is eliminated and the production of the lipid peroxide is inhibited, it will be possible to prevent the reduction of tissue function and the necrosis of the tissue to thereby make the treatment and prophylaxis for various diseases possible.

Various agents for eliminating the active oxygen species or antioxidants have been proposed. However, these agents are not very effective for the treatment and prophylaxis of ischemia-reperfusion injury.

Hence, there is strong and urgent need for the development of a medicament for the treatment or prophylaxis of the ischemia-reperfusion injury.

SUMMARY OF THE INVENTION

An object of the present invention is to provide an effective medicament for the treatment or prophylaxis of the ischemia-reperfusion injury.

The present invention provides a method for the treatment or prophylaxis of ischemia-reperfusion injury which comprises administering an effective amount of batroxobin to a patient.

The present invention also provides a method for the treatment or prophylaxis of ischemia-reperfusion injury which comprises administering an effective amount of batroxobin to a patient with ischemic myocardial reperfusion injury.

The present invention further provides a method for the treatment or prophylaxis of ischemia-reperfusion injury which comprises administering an effective amount of batroxobin to a patient with ischemiac cerebral reperfusion injury.

The inventors of this invention have discovered that batroxobin is effective for the treatment or prophylaxis of restenosis and arterial sclerosis after percutaneous transluminal angioplasty (PTA) and filed a patent application based on the discovery (U.S. Ser. No. 08/555,451, U.S. Pat. No. 5,595,974 ).

They have further conducted various studies with respect to batroxobin on its pharmaceutical effects. Using an animal model, they have discovered that batroxobin inhibits cellular injury associated with ischemia-reperfusion injury, and completed the present invention.

Batroxobin used in the present invention is a thrombin-like enzyme, preferably derived from snake (Bothrops atrox moojeni) venom and its formulation is commercially available under batroxobin formulation from Tobishi Pharmaceutical Co., Ltd.

The medicament of the present invention is used for the treatment or prophylaxis of the ischemia-reperfusion injury in myocardial disease, cerebrovascular disorder, kidney disease, liver disease, lungs disease, pancreas disease and the like, or in organ transplantation.

Recently, percutaneous transluminal coronary revascularization (PTCR) and percutaneous transluminal coronary angioplasty (PTCA) have broadly been conducted for decreasing myocardial necrosis in cardiac infarction. The medicament of the present invention is effective not only for myocardiopathy which occurs when blood flow is restarted after such operations, but also for neurocyte disorder occurring in cerebral ischemic disorder when blood flow is restarted.

The components and their contents in 1 ml of batroxobin formulation (a thrombin-like enzyme derived from snake (Bothrops atrox moojeni) venom) are as follows:

| | |
|---|---|
| batroxobin (main component) | 10 BU |
| chlorobutanol (preservative) | 3 mg |
| gelatin hydrolyzate (stabilizer) | 0.1 mg |
| sodium chloride (isotonic agent) | 9 mg |
| distilled water for injection | to 1 ml |

The dosage of batroxobin employed in the present invention is dependent on conditions of a patient. In general, the dosage is in the range of from 1 to 20 batroxobin units (hereinafter, abbreviated as BU) for adult per day, although the dosage outside the above range can be used depending on the conditions of the patient.

Batroxobin may be suitably diluted and administered in the form of drip or injection, intravenously, intraarterially or topically. The batroxobin unit described herein is a unit representing an enzymatic activity of batroxobin and such an activity that the coagulation of plasma is taken place in $19.0 \pm 0.2$ seconds when 0.1 ml of a batroxobin solution is added to 0.3 ml of standard human plasma containing citric acid at a temperature of 37° C. is defined as 2 BU.

Acute toxicity test for batroxobin was conducted by intravenous administration to mice, rats, rabbits and dogs. The resulted $LD_{50}$ values (BU/kg) were as follows:

| kinds of animal | $LD_{50}$ value (BU/kg) |
|---|---|
| mice (ddY strain) | 192~210 |
| rats (Wistar strain) | 105~110 |
| rabbits (NW species) | >300 |
| dogs (hybrid) | 190~208 |

DESCRIPTION OF THE PREFERRED EMBODIMENTS

The present invention will hereunder be described in more detail with reference to the following Examples, but it should be understood that the present invention is not limited thereto.

EXAMPLE 1

Effects of batroxobin for the treatment or prophylaxis of ischemia-reperfusion injury in myocardial reperfusion model of dogs.

Experimental method 30 mg/kg of sodium pentobarbital was administered intravenously to each of 10 male and female dogs having 8 to 12 kg weights to anesthetize them. After anesthesia was conducted, trachea insertion was conducted immediately followed by respiration. After thoracotomy was conducted by excising a portion between third and forth costas, the heart was exposed by breaking pericardium. Ischemia was provided by desquamating ramus desendens in front of left coronary from ambient tissue and stopping temporarily blood circulation by ligating it with an occluder. During the experiment, the stop of a blood flow was recognized by monitoring the amount of coronary blood flow, electrocardiogram and left venticle pressure. The reperfusion was then followed by removing the ligation. The evaluation of ischemia-reperfusion injury was conducted as described detail in the following explanation. Blood circulation was re-started 90 minutes after ligation and after 30 minutes, the heart was stopped by injecting immediately 10 ml of saturated potassium chloride solution. After perfusing retrogradely phosphate buffer from arteria subclavia to the heart, the stenosis site was ligated again and then non-ischemia region was stained by perfusing to the heart 10 ml of 2% Evans blue solution in phosphate buffer. Thereafter, the heart was extracted and cut horizontally at a thickness of 1cm, and the cut heart was placed in 1% T0 (Triphenyl Tetrazolium Chloride) and stained. Then, the each area of Evans blue stained positive region (blue: non-ischemia area), Evans blue stained negative and TTC stained positive region (red: coronary ischemia healthy and normal area) and Evans blue stained negative and TTC stained negative region (white: cardiac infarction area) in the cross section of the cut heart was measured by planimeter. Then, the ischemia volume and the infarction volume were found from the area measured as described above and the thickness of each tissues whereby the percentage of infarction volume/ischemia volume ratio was calculated. In addition, in the group which batroxobin is administered (n=5), 0.5 BU/kg of batroxobin was administered through the common jugular vein at 30 minutes before starting the reperfusion of a blood flow, and in the control group (n=5), saline was administered similarly at the same volume.

Results

The percentage of infarction volume/ischemia volume ratio of the control group was 47±10%. The percentage of infarction volume/ischemia volume ratio of the batroxobin administering group was 25±5%. The results show that batroxobin inhibits significantly ($p<0.005$) the extension of necrosis in cardiac infarction area (Table 1). Therefore, it was found that the administration of batroxobin suppress the myocardial ischemia-reperfusion injury.

TABLE 1

| Specimen | Number | infarction volume/ischemia volume ratio (%) |
|---|---|---|
| Control | 5 | 47 ± 10 |
| Batroxobin | 5 | 25 ± 5** |

**$p < 0.005$.

EXAMPLE 2

Effects of batroxobin for the treatment and prophylaxis of ischemia-reperfusion injury in cerebral ischemia-reperfusion model of rats.

Experimental method

18 Wistar male rats weighing about 200 to 250 g were divided into three groups wherein each group is consisted of 6 rats and referred to as a pseudo-operating group, a control group and a batroxobin administering group, respectively. After the rat was anesthetized with 10% chloral hydrate (350 mg/kg), the rat was fixed in stereotaxic operation apparatus and both sides alar ostia were exposed and both sides arteria vertebralis were shut down by electro heat-coagulating method. After 24 hours, cervical region median was excised under the same anesthesia condition as described above and both sides common carotid artery (CCA) were extracted. The extract was clamped by a clamp which does not give a damage for 30 minutes while monitoring brain wave.

The electrodes by which the brain wave is received were attached: one electrode to frontnasal median site, and the other to parietal region whereby the monitoring was conducted. At 30 minutes after the CCA was closed, the clamp was taken off again and cerebral perfusion was conducted for 6 hours. After the reperfusion was terminated, the head of the rat was cut and the brain was delivered and fixed by formalin. After embedding the brain with paraffin, frontal cut pieces across hippocumpus were provided by cutting the brain into thin slices and then hematoxylin and eosin stain was applied to stain those samples. The degree of injury of tissues was evaluated by observing the samples under optical microscope and calculating each of normal pyramidal cell and injured pyramidal cell per 1 mm of length of hippocumpus CAl.

8 BU/kg of batroxobin was administered abdominally to the batroxobin administering group at 30 minutes before clamping the CCA.

The saline of the same volume was administered to the control group. In the pseudo-operating group, both sides alar ostia were exposed and after 24 hours, the CCA was exposed, but the saline of the same volume was administered at 30 minutes before exposing the CCA, without coagulating or clamping.

Results

Pseudo-operating group

By observing under optical microscope, there were no any abnormal observations. The survival rate of hippocumpus CA1 greater petrosal cell was 98.5±1.6% (Table 2).

Control group

By observing under optical microscope, atrophia of greater petrosal cell in hippocumpus CA1 was observed and the degree of the stain of cytoplasm was deep. In addition, cell nucleus was concentrated in the form of triangle and the spaces between the cells were increased. The survival rate of hippocumpus CA1 greater petrosal cell was 56.4±19.8% (Table 2).

Batroxobin administering group

By observing under optical microscope, atrophia of greater petrosal cell in hippocumpus CA1 was only slightly observed. The cytoplasm was only slightly stained. Cell nucleus and nucleolus were normal. The spaces between cells were also normal. The survival rate of hippocumpus CA1 greater petrosal cell was 87.3±5.4%, which is significant as compared with the control group ($p<0.01$) (Table 2).

Thus, the cell injury caused by cerebral ischemia-reperfusion was inhibited significantly by the batroxobin administration. Accordingly, it has been found that batroxobin has an effect to inhibit cerebral ischemia-reperfusion injury.

TABLE 2

Effects of batroxobin on the survival rate of hippocumpus CA1 greater petrosal cell after cerebral ischemia-reperfusion

| Group | the number of rats | survival rate (%) |
|---|---|---|
| Pseudo-operating | 6 | 98.5 ± 1.6 |
| Control | 6 | 56.4 ± 19.8[1] |
| Batroxobin | 6 | 87.3 ± 5.4[2] |

The survival rate is expressed by the average ± S. D.
[1] Comparison with pseudo-operating group, $p < 0.01$.
[2] Comparison with control group, $p < 0.01$.

Whereas particular embodiments of the invention have been described above for purposes of illustration, it will be appreciated by those skilled in the art that numerous variations of the details may be made without departing from the invention as described in the appended claims.

What is claimed is:

1. A method for the treatment or prophylaxis of ischemia-reperfusion injury which comprises administering an amount of batroxobin to a patient at risk of ischemia-reperfusion injury caused by a medical procedure, wherein the amount is effective in alleviating or preventing the injury.

2. The method of claim 1, wherein the amount of batroxobin is administered to a patient with ischemic myocardial injury.

3. The method of claim 1, wherein the amount of batroxobin is administered to a patient with ischemic cerebral injury.

4. The method of claim 1, wherein the amount of batroxobin is in the range of from 1 to 20 BU per day.

* * * * *